United States Patent [19]

Leffler

[11] Patent Number: 4,966,166

[45] Date of Patent: Oct. 30, 1990

[54] PROPHYLACTIC DEVICE AND METHOD

[76] Inventor: John T. Leffler, 8043 Tierneys Woods Curve, Bloomington, Minn. 55438

[21] Appl. No.: 228,397

[22] Filed: Aug. 4, 1988

Related U.S. Application Data

[63] Continuation-in-part of Ser. No. 100,923, Sep. 28, 1987, abandoned.

[51] Int. Cl.⁵ .............................................. A61F 6/04
[52] U.S. Cl. .................................... 128/844; 128/842; 128/918
[58] Field of Search .................. 128/842, 844, 918; 604/347, 349, 352, 385 R, 385 A, 389

[56] References Cited

U.S. PATENT DOCUMENTS

| | | | |
|---|---|---|---|
| D. 254,808 | 4/1980 | Meldahl | 128/844 X |
| 3,526,227 | 9/1970 | Appelbaum | 604/350 |
| 3,536,066 | 10/1970 | Ludwig | 128/844 X |
| 3,976,076 | 8/1976 | Beach | 604/349 X |
| 4,004,591 | 1/1977 | Freimark | 604/330 |
| 4,349,026 | 9/1982 | Miyata | 128/844 X |
| 4,626,286 | 12/1986 | Lubbs | 128/837 X |
| 4,713,066 | 12/1987 | Komis | 604/349 X |
| 4,735,621 | 4/1988 | Hessel | 128/844 X |
| 4,798,600 | 1/1989 | Meadows | 128/839 X |
| 4,805,604 | 2/1989 | Spery | 128/844 X |

FOREIGN PATENT DOCUMENTS

| | | | |
|---|---|---|---|
| 36015 | 1/1901 | European Pat. Off. | 604/349 |
| 162728 | 9/1905 | Fed. Rep. of Germany | 604/349 |
| 1807884 | 7/1969 | Fed. Rep. of Germany | 604/349 |
| 2060233 | 6/1972 | Fed. Rep. of Germany | 128/844 |
| 2349361 | 4/1975 | Fed. Rep. of Germany | 604/349 |
| 938465 | 10/1963 | United Kingdom | 604/349 |

OTHER PUBLICATIONS

Gee Bee, A New Method for the Profession, 8/1934.

*Primary Examiner*—Robert A. Hafer
*Assistant Examiner*—Kevin G. Rooney
*Attorney, Agent, or Firm*—Dorsey & Whitney

[57] ABSTRACT

A tubular prophylactic device and method is disclosed which provides for frictional stimulation of the male penis during copulation while simultaneously serving as an impermeable barrier for the prevention of disease and for birth control purposes. In one form the device consists of a pleated collapsible tube with an extended length from the open end to the closed end of at least approximately twice the length of the erect mature human male penis. The additional length allows the penis to move relative to the prophylactic device during copulation, with the prophylactic device remaining stationary with respect to the wall of the female vagina. In another form the device is characterized by an inwardly folded sleeve that engages the penis and provides for sealing and an excess length that allows for movement of the end of the penis relative to the device when in use.

The method is characterized by relative movement between the glans of the penis and the membrane of the device during use thereof.

2 Claims, 4 Drawing Sheets

Fig. 5B
Fig. 5A
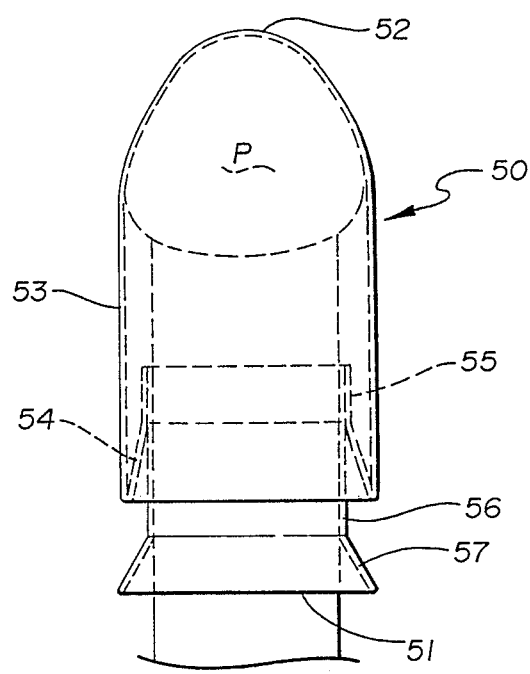
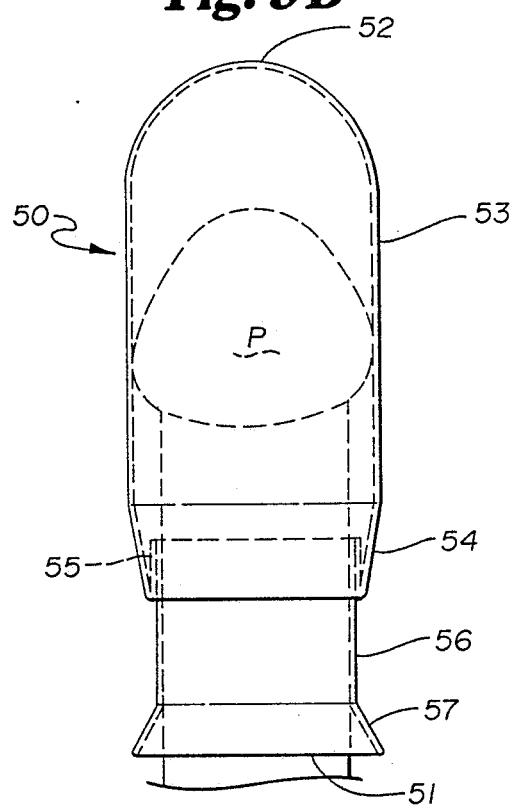
Fig. 5C
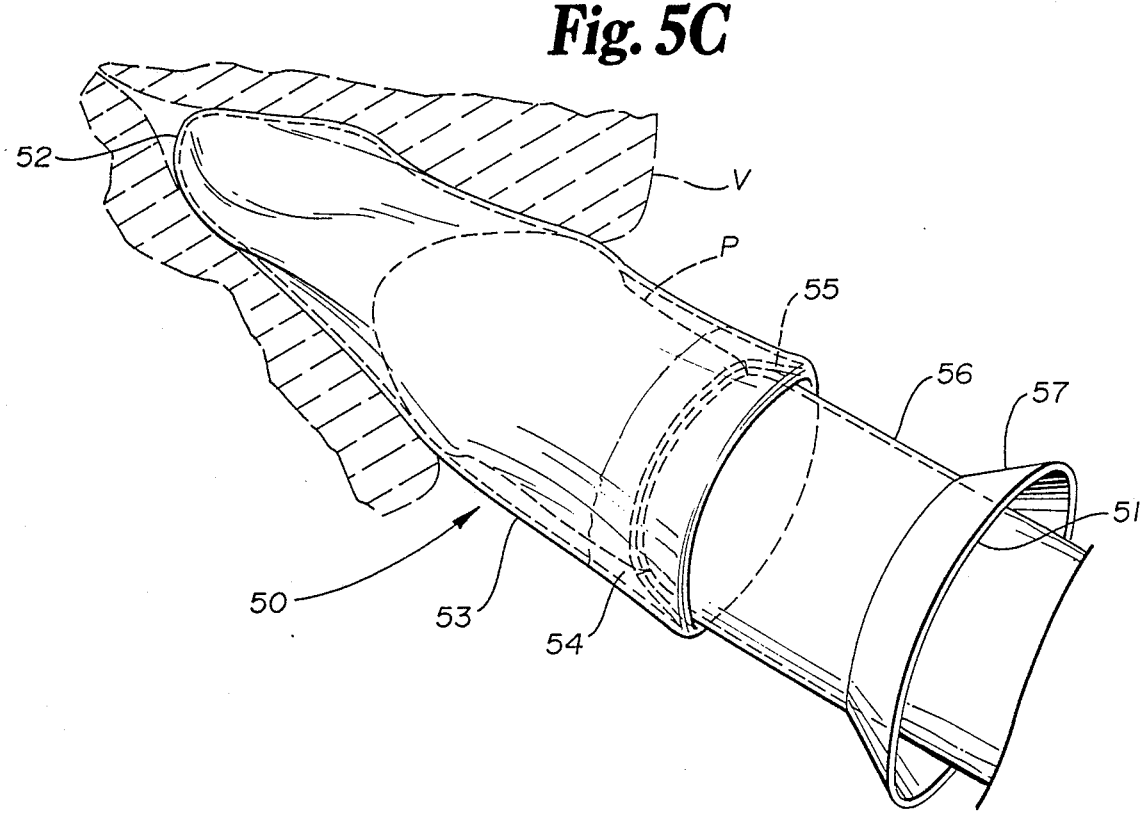

PROPHYLACTIC DEVICE AND METHOD

This is a continuation-in-part of application Ser. No. 100,923, filed Sept. 28, 1987 now abandoned.

TECHNICAL FIELD

This invention pertains to a prophylactic device and method. In particular, it pertains to a prophylactic device that serves as a barrier for disease prevention such as Acquired Immune Deficiency Syndrome (AIDS), and for birth control and which is formed of thin elastic sheet material in a conventional tubular configuration, with an open end and a closed end. The device provides for a method of accomplishing the foregoing while closely simulating copulation without such a device.

BACKGROUND ART

Prophylactic devices for preventing the transmission of venereal and other diseases and for birth control, which isolate the human male penis from the human female vagina and cervix, are well known. In its typical embodiment, the prophylactic device provides a sheathing that is affixed to and surrounds the penis and moves with the penis within the vagina during copulation. The prior art devices limit friction on the penis and lessen male stimulation in that the penis does not move with respect to the wall of the device. This has long been an objection to the use of prophylactic devices and is a long-felt need in the art. A prophylactic device that provides for direct frictional stimulation to the penis, thereby more closely simulating copulation without a prophylactic device, while simultaneously serving as a barrier, would be a significant advancement and fill a long-felt need.

SUMMARY OF THE INVENTION

The present invention comprises a prophylactic device that provides for direct frictional stimulation o the penis during copulation.

One embodiment of the device comprises a collapsible tube open at one end and closed at the opposite end. The collapsible tube is formed from a thin, impermeable, elastic material and has a diameter substantially equal to or greater than that of an erect mature human male penis and a length of at least approximately twice the length of the erect mature human male penis. The collapsible tube includes sealing means on the open end in the form of a truncated conical section. The truncated conical section may include adhesive for securing the device to the penis. The adhesive is covered by a peel-away liner, allowing the penis to be inserted into the prophylactic without contact between the penis and the adhesive.

A second embodiment of the device is characterized by an inwardly folded sleeve section that provides for sealing and prevents unwanted removal during use by fitting snugly around the penis. In the second embodiment means is provided on or at the sleeve section for preventing an unfolding or peeling away of the inward fold of the sleeve section during use, thereby preventing unwanted removal and maintaining the sealing relationship with the penis.

In use, the collapsed tube is fitted over the penis and the truncated conical section or the inwardly folded sleeve section forms a seal with the penis. If adhesive is used, the peel-away liner is removed and the prophylactic is adhered to the penis. As the penis is inserted into the vagina the prophylactic contacts the wall of the vagina. As the penis is withdrawn, the excess length of the device (that portion of the length that exceeds the length of the erect penis when the device is in place) remains seated in the vagina and the end portion of the penis moves relative to the device. When the penis is reinserted in the opposite direction, it also slides within the device, resulting in direct friction on the penis as it moves relative to the wall of the prophylactic device, thereby more closely simulating copulation without a prophylactic device. The relative movement between the penis and the inner wall of the prophylactic device during copulation characterizes the method of the invention.

BRIEF DESCRIPTION OF THE DRAWINGS

FIG. 5A is a top view of a variation of the embodiment of FIGS. 4A and 4B with the device fitted on an erect male penis before insertion into the vagina;

FIG. 5B is a top view of the device of FIG. 5A after insertion of the penis and device into the vagina and withdrawal at the limit of the withdrawal stroke;

FIG. 5C is a perspective view of the prophylactic device of FIG. 5A after insertion and withdrawal at the limit of the withdrawal stroke;

DETAILED DESCRIPTION

Figure 1:
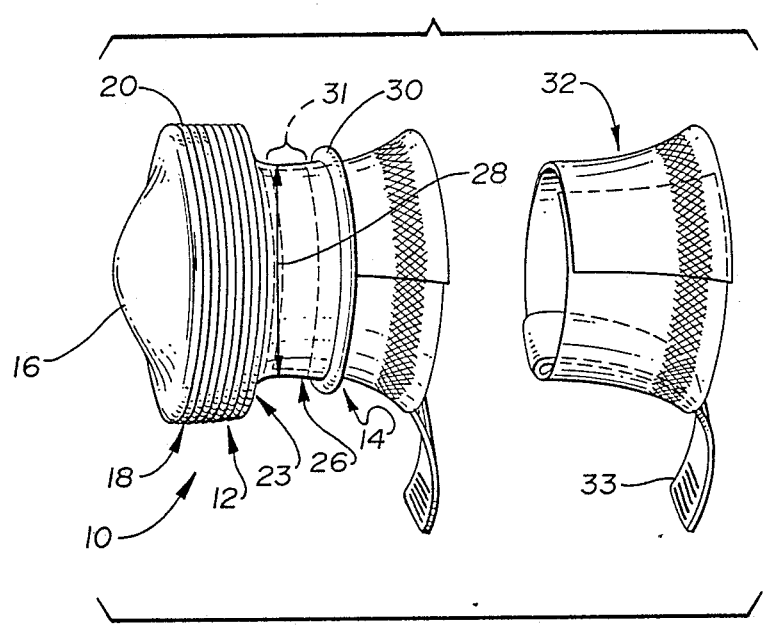
FIG. 1 is a side view of a prophylactic device showing the pleated collapsed tube with the peel-away liner, which comprises one embodiment of the present invention.
Figure 2:
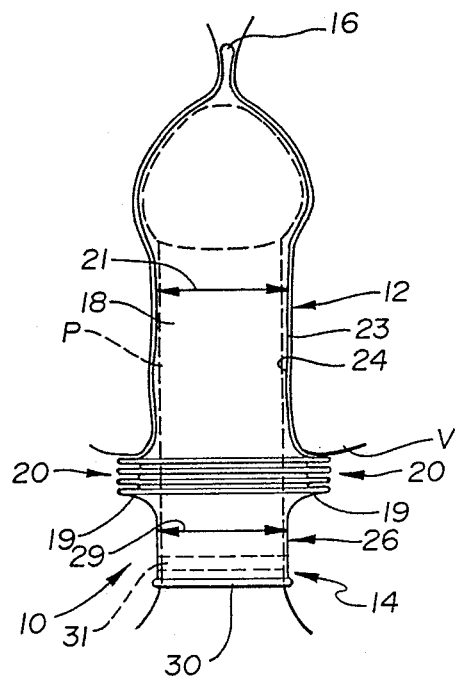
FIG. 2 is a top view of the device shown in FIG. 1, with the prophylactic device fitted on an erect human male penis and with the device and penis inserted in a human female vagina.
Figure 3:
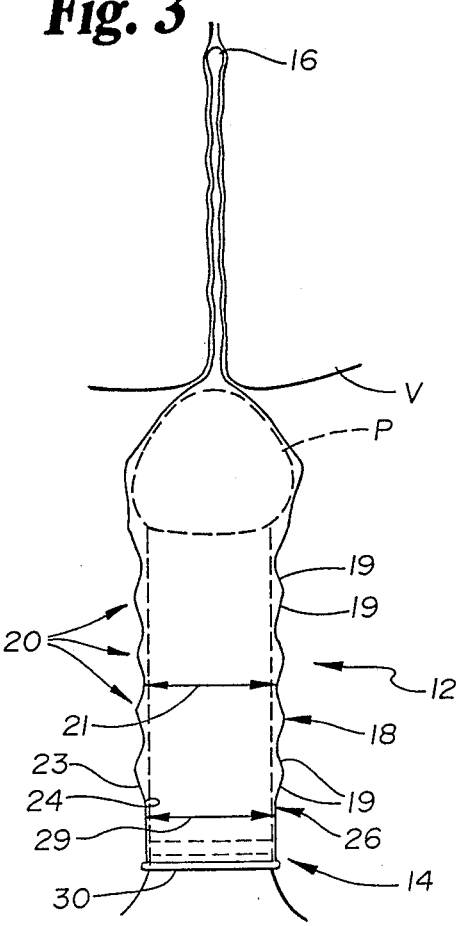
FIG. 3 is a top view similar to FIG. 2 showing the penis when withdrawn from the vagina with the end of the device seated in the vagina.

Referring to the FIGS. 1-3, one embodiment of the present invention consisting of a prophylactic device 10 comprising a collapsible tube 12 formed with a thin impermeable elastic material is shown. Latex rubber with a thickness of approximately 0.002 inches is a suitable substance. The collapsible tube 12 includes an open end 14, a closed end 16 and a midsection 18.

The midsection 18 is formed with a plurality of fan-folds or pleats 20. The pleats 20 are shown in their collapsed state in FIG. 1 and in their expanded state in FIG. 3. Each pleat 20 is formed by two opposed and opposite frusto-conical sections 19. With all the pleats fully extended, the prophylactic device 10 has a maximum length of approximately twice the length of an erect mature male penis, P. In practice a suitable length is seven to fourteen inches. The midsection 18 has a relaxed diameter 21 substantially equal to or greater than the diameter of the erect mature male penis, P. In practice a suitable relaxed diameter is one to two inches. A conventional lubricant (not shown) is provided on the inner wall of the device. The midsection 18 has an outer wall 23 and an inner wall 24.

The open end 14 consists of a truncated conical section 26. The truncated conical section 26 has a minimum diameter 28 slightly less than the diameter of the mature male penis, P. The truncated conical section 26 includes a rolled lip 30. An optional adhesive band 31 may be included in the truncated conical section 26 and covered with a peel-away liner 32 having a liner pull tab 33.

In operation, the mature male penis, P, is inserted into the prophylactic device 10. The truncated conical section 26 forms a seal around the base of the penis 22. The truncated conical section 26 fits tightly around the base of the penis 22 as the truncated conical section 26 minimum diameter 28 is forced to expand to an enlarged diameter 29 by the slightly larger diameter mature male penis, P. The thin impermeable elastic material urges the truncated conical section 26 back to its original diameter 28 thereby affixing and sealing the prophylactic device 10 to the base of the penis, P. An adhesive band 31 may also be used to affix the prophylactic deivce 10 to the base of the penis, P. Once the penis is inserted in the prophylactic device the peel-away liner 32 may be removed with the liner pull tab 33.

Referring to FIG. 2, after the penis, P, is inserted into the vagina, V, during withdrawl, the lubricant in the prophylactic device 10 allows the penis, P, to move relative to the prophylactic device 10 while the prophylactic device 10 remains seated in the vagina, V. As depicted in FIGS. 2 and 3, the pleats 20 which extend in accordian-like fashion along the length of the midsection 18, allow the collapsible tube 12 to expand and contract as the penis moves within the vagina and the prophylactic device 10, while the prophylactic device 10 remains approximately stationary with respect to the vagina, V.

Figure 4B:
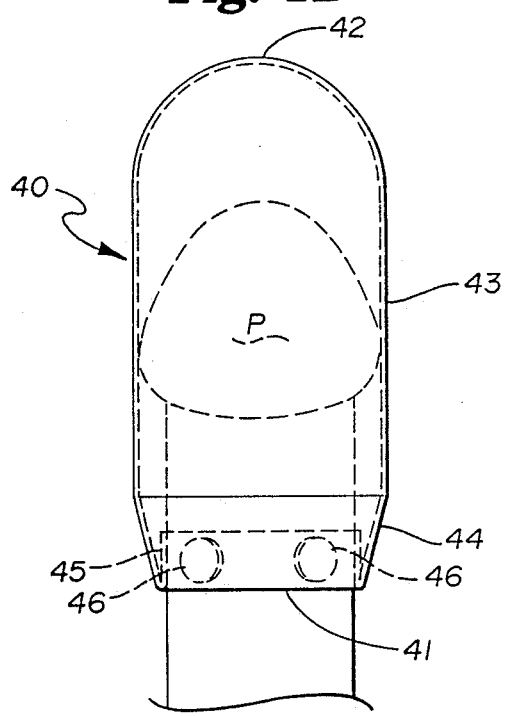
FIG. 4B is a top view of the prophylactic device of FIG. 4A after insertion of the penis and device into the vagina and withdrawal at the limit of the withdrawal stroke.
Figure 4A:
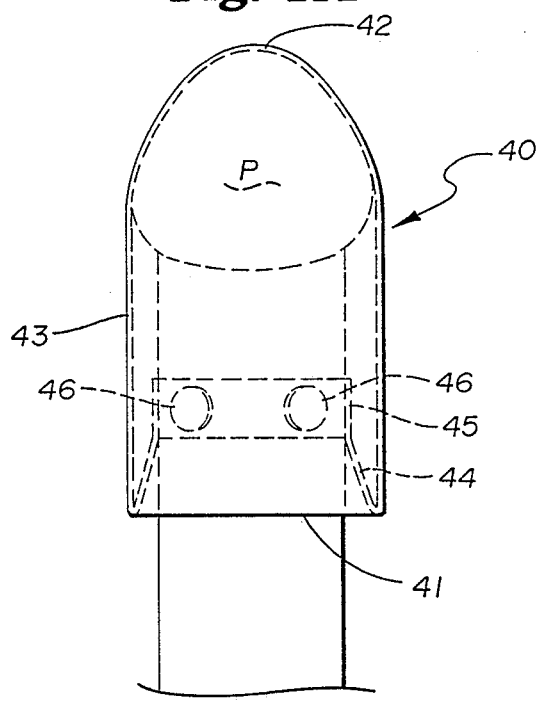
FIG. 4A is a top view of a second embodiment of the prophylactic device of the present invention and shows the device fitted on an erect male penis before insertion into the vagina.
Figure 4C:
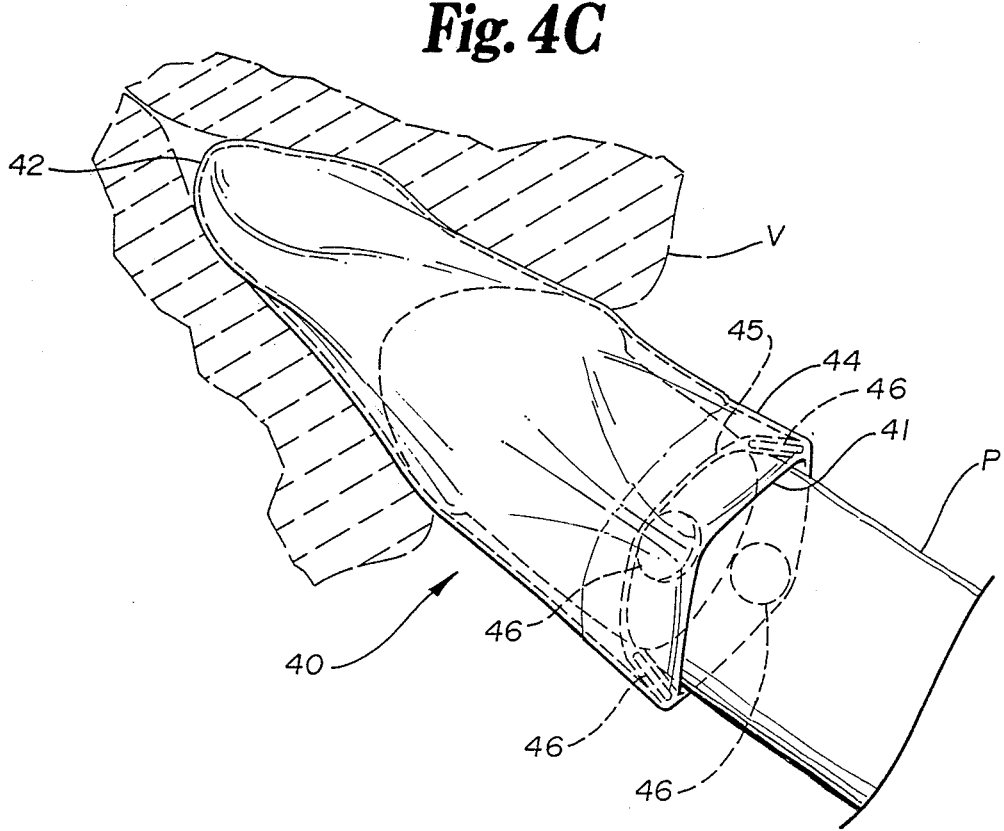
FIG. 4C is a perspective view of the prophylactic device of FIG. 4A after insertion and withdrawal at the limit of the withdrawal stroke.
Figure 6B:
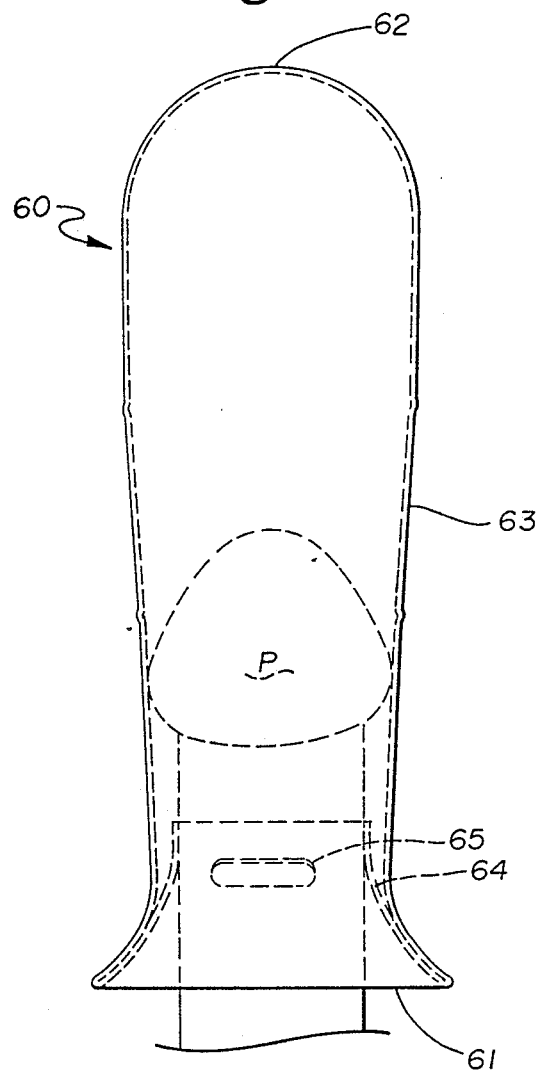
FIG. 6B is a top view of the device of FIG. 6A after insertion of the penis and device into the vagina and withdrawal at the limit of the withdrawal stroke.
Figure 6A:
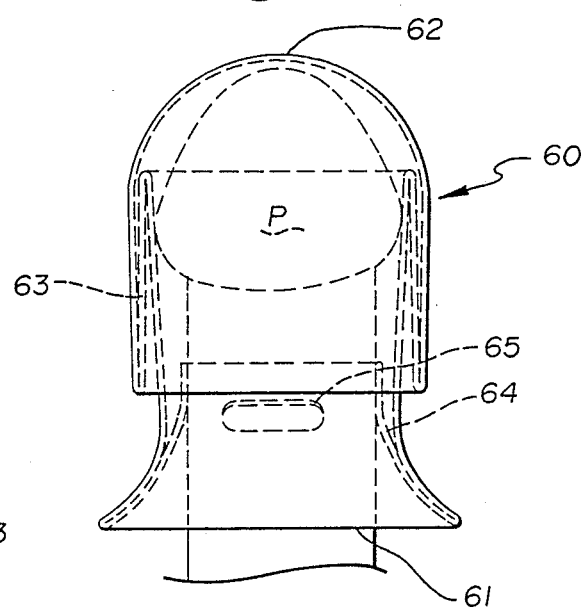
FIG. 6A is a top view of another variation of the embodiment of FIGS. 4A and 4B with the device fitted on an erect male penis before insertion into the vagina.

A second embodiment of the present invention, characterized by an inwardly folded sleeve section, is shown in FIGS. 4A, 4B and 4C, and with modifications in FIGS. 5A, 5B and 5C in FIGS. 6A and 6B.

The second embodiment is shown fitted on an erect male penis before insertion into the vagina in FIG. 4A, after insertion in FIG. 4B, and after withdrawal in FIG. 4C. With reference to FIGS. 4A, 4B, and 4C prophylactic device 40 has an open end 41, a closed end 42, a midsection 43, and a truncated section 44. A cylindrical sleeve 45, integrally formed from the sheet material that forms prophylactic 40, is folded inwardly at opening 41. Four relatively rigid thin plastic discs 46 are adhered to the outwardly facing surface of sleeve 45 as shown. Rigid discs 46 serve to prevent sleeve 45 from being rolled over on itself, thereby lowering the resistance to removal of prophylactic 40 from penis, P, in a manner described more particularly below.

The embodiment of FIGS. 4A, 4B and 4C is formed of impermeable thin sheet material, as is well known in the art, and has the following typical dimensions, which achieve the desired results with a typical erect male penis. The overall length of the prophylactic 40 from open end 41 to closed end 42 is four to five inches. The diameter of mid-section 43 is one and one-half to one and three-fourths inches. The diameter of opening 41 is one to one and one-half inches. The altitude of truncated section 44 is about three-fourths inch and the diameter of discs 46 is about three-sixteenths inch, with sleeve 45 about one-fourth inch in altitude or height.

In general, the dimensions of prophylactic 40 are chosen so that there is a snug, sealing fit of sleeve 45 around the shaft of penis, P, and a loose fit of midsection 43 about penis, P, including the glans thereof, to achieve the requisite relative movement of the penis, P, with respect to the wall of midsection 43 of prophylactic 40 during copulation, responsive to the long-felt need in the art. The specific dimensions may vary from those specified to achieve the desired result.

In use, the embodiment of FIGS. 4A, 4B and 4C is fitted onto an erect male penis, P, as shown in FIG. 4A. Sleeve section 45 is positioned on the shaft of penis, P, so as to leave a substantial distance from the tip of penis, P, to the closed end 42 of prophylactic device 40. When penis, P, and prophylactic 40 are inserted into the vagina in use, penis, P, moves into engagement with closed end 42 as truncated section 44 rolls over itself, and the portion of penis, P, from sleeve section 45 to the tip thereof moves relative to the wall of midsection 43 of prophylactic device 40. The limits of this movement are shown in FIGS. 4A and 4B.

In moving from the position of FIG. 4B to the position of FIG. 4C there is some tendency, because of frictional forces, to pull prophylactic 40 off penis, P. This result is extremely undesirable and to insure that it does not occur rigid discs 46 are adhered to the outwardly facing wall of sleeve 45. In the absence of discs 46, the thin flexible sheet material that forms phrophylactic 40 can fold or peel over itself beginning at the fold at opening 41 and extending through the height of sleeve 45, thereby peeling sleeve 45 from its position as prophylactic 40 is pulled off penis, P. Rigid discs 46 prevent the folding over on itself or peeling of sleeve 45 in that when the fold line in sleeve 45 reaches the periphery of discs 46, further pulling requires a tilting or lifting up of the edge of discs 46 in order to continue with the peeling process. This is shown in somewhat exaggerated form in FIG. 4C in which discs 46 are shown fitting outwardly at the point of engagement with the fold at opening 41. Discs 46 are prevented from flipping over by the resiliency or lack thereof of the sheet material that forms prophylactic 40. Consequently, discs 46 prevent further folding over on itself or peeling of sleeve 45. This means that sleeve 45 can be pulled off only by overcoming the frictional force at the interface with penis, P, and this frictional force is sufficient to prevent removal of prophylactic device 40.

Thus, in use, prophylactic device 40 provides for movement of penis, P, with respect to the wall of midsection 43, back and forth, between the positions of FIG. 4B and the position of FIG. 4C. This more closely simulates copulation without any barrier or prophylactic device and, at the same time, provides for a secure, reliable seal or protective barrier beeween partners for birth control purposes and to prevent the transmission of disease.

A modification of the embodiment of FIGS. 4A, 4B and 4C is shown in FIGS. 5A, 5B and 5C. With reference to FIGS. 5A and 5B, prophylactic device 50 includes an open end 51, a closed end 52, a midsection 53, an intermediate truncated section 54, a double ply sleeve section 55, a neck section 56 and a terminal truncated section 57.

The size, configuration and functioning of the modified design of FIGS. 5A, 5B and 5C is similar to that of the embodiment of FIGS. 4A, 4B and 4C, except that the modification of FIGS. 5A, 5B and 5C has a welded two-ply sleeve section, no rigid disc structure, an extended neck section 56 and a flared or truncated terminal section 57.

With the modified design of FIGS. 5A, 5B and 5C, relative movement between penis, P, and midsection 53 of prophylactic device 50 occurs as shown in FIGS. 5A, 5B and 5C. Pulling off of prophylactic device 50 from penis, P, is prevented by the double-ply, extra resiliency or strength in sleeve 55 and the increased frictional force due to the increased area of snug engagement with the shaft of penis, P, extending through neck section 56. This is best seen in FIG. 5C in which the double-ply construction of sleeve 55 can be seen to resist at edge 58 peeling of double-ply sleeve section 55, aided by neck section 56.

In the modification shown in FIGS. 6A and 6B, prophylactic device 60 includes an open end 61, a closed end 62, a midsection 63, which is pleated or folded over on itself, and a truncated sleeve section 64. Truncated sleeve section 64 includes a welded, two-ply portion near opening 61 and a single-ply portion to which two rigid tabs 65 are adhered. Tabs 65 function in the same manner as discs 46 in prophylactic device 40 in preventing the unwanted removal or peeling-off of prophylactic device 60 during use. Thus, truncated sleeve 64 combines the features of the embodiment of FIGS. 4A and 4B and the modification of FIGS. 5A and 5B in that both a rigid tab structure and a double-ply sleeve structure is provided to prevent unwanted removal of the prophylactic device 60.

In each of the designs of FIGS. 4A, 4B and 4C; 5A, 5B and 5C and 6A and 6B, a lubricant can be provided inside the prophylactic device; however, lubrication on the snugly fitting portion of the device that engages the shaft of the penis is not desirable. To confine lubication to only that portion of the device in which relative movement of the penis with respect to the device is desired, a breakable seal can be provided at the inside terminal edge of sleeve section 45 (in a flattened state) in the design of FIG. 4A, 4B, and 4C at the inside terminal edge of sleeve 55 in the design of FIGS. 5A, 5B and 5C, and at the inside terminal edge of truncated sleeve 64 in the design of FIGS. 6A and 6B, after lubricant has been applied to the inner-wall, midsection area of the respective devices. The seal is broken when the device is applied for use.

Unlike prior prophylactic devices, the present invention thus provides for relative movement between the penis and the prophylactic device and direct frictional stimulation of the penis on both the insertion stroke and the withdrawal stroke, thereby simulating copulation without a prophylactic device, while retaining the disease prevention and birth control functions of the prior art devices.

Having thus described the invention, the following is claimed:

1. A tubular prophylactic device formed of flexible, thin impermeable sheet material, having an open end, a closed end and an extended length from the open end to the closed end, characterized by:
   a. a midsection extending between the open end and the closed end having a circumference sufficiently large to permit movement of an erect male penis within said midsection during coitus,
   b. a sleeve section formed at the open end having a circumference sufficiently small to fit snugly about the shaft of an erect mature human penis, folded inwardly with respect to the midsection, thereby being disposed inside the device for fixed engagement with the shaft of the penis, and
   c. a plurality of circumferentially spaced, thin rigid members adhered to the sleeve section on the outer surface thereof between the sleeve section and the midsection to prevent peeling of the sleeve section from the shaft of the penis.

2. The device of claim 1 wherein the inside of the midsection of the device is lubricated and wherein the inside edge of the sleeve section is closed and releasably sealed to itself thereby separating the lubicated inside of the midsection from the inside surface of the sleeve section.

* * * * *